United States Patent
Zhang et al.

(10) Patent No.: US 10,853,941 B2
(45) Date of Patent: Dec. 1, 2020

(54) REGISTRATION METHOD AND SYSTEM FOR NON-RIGID MULTI-MODAL MEDICAL IMAGE

(71) Applicant: HUAZHONG UNIVERSITY OF SCIENCE AND TECHNOLOGY, Hubei (CN)

(72) Inventors: Xuming Zhang, Hubei (CN); Fei Zhu, Hubei (CN); Jingke Zhang, Hubei (CN); Jinxia Ren, Hubei (CN); Feng Zhao, Hubei (CN); Guanyu Li, Hubei (CN); Mingyue Ding, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 119 days.

(21) Appl. No.: 16/094,473

(22) PCT Filed: Oct. 9, 2016

(86) PCT No.: PCT/CN2016/101547
§ 371 (c)(1),
(2) Date: Oct. 18, 2018

(87) PCT Pub. No.: WO2018/000652
PCT Pub. Date: Jan. 4, 2018

(65) Prior Publication Data
US 2019/0130572 A1     May 2, 2019

(30) Foreign Application Priority Data

Jun. 30, 2016  (CN) .......................... 2016 1 0506619

(51) Int. Cl.
*G06T 7/00*       (2017.01)
*G16H 30/40*   (2018.01)
(Continued)

(52) U.S. Cl.
CPC .......... *G06T 7/0016* (2013.01); *G06T 3/0068* (2013.01); *G06T 3/60* (2013.01);
(Continued)

(58) Field of Classification Search
CPC ... G06T 7/0016; G06T 3/0068; G06T 11/005; G06T 11/006; G06T 2207/10081;
(Continued)

(56) References Cited

U.S. PATENT DOCUMENTS

2008/0040077 A1 *  2/2008  Dean .................... G01M 11/005
                                                                  702/190

FOREIGN PATENT DOCUMENTS

CN              103345741             10/2013

OTHER PUBLICATIONS

El-Gamal, F.E.Z.A., Elmogy, M. and Atwan, A., 2016. Current trends in medical image registration and fusion. Egyptian Informatics Journal, 17(1), pp. 99-124.*
(Continued)

*Primary Examiner* — Zhitong Chen
(74) *Attorney, Agent, or Firm* — JCIPRNET

(57) ABSTRACT

The present invention discloses a registration method and system for a non-rigid multi-modal medical image. The registration method comprises: obtaining local descriptors of a reference image according to Zernike moments of order 0 and repetition 0 and Zernike moments of order 1 and repetition 1 of the reference image; obtaining local descriptors of a floating image according to Zernike moments of order 0 and repetition 0 and Zernike moments of order 1 and repetition 1 of the floating image; and finally obtaining a registration image according to the local descriptors of the reference image and the floating image. In the present, by using self-similarity of the multi-modal medical image and adopting the Zernike moment based local descriptor, the (Continued)

non-rigid multi-modal medical image registration is thus converted into the non-rigid mono-modal medical image registration, thereby greatly improving its accuracy and robustness.

11 Claims, 8 Drawing Sheets

(51) Int. Cl.
 *G06T 3/00* (2006.01)
 *G06T 3/60* (2006.01)
 *G06T 11/00* (2006.01)
(52) U.S. Cl.
 CPC .............. *G06T 7/00* (2013.01); *G06T 11/005* (2013.01); *G06T 11/006* (2013.01); *G16H 30/40* (2018.01); *G06T 2207/10081* (2013.01); *G06T 2207/10088* (2013.01); *G06T 2207/10104* (2013.01); *G06T 2207/20048* (2013.01); *G06T 2207/20221* (2013.01)
(58) Field of Classification Search
 CPC . G06T 2207/10088; G06T 2207/10104; G06T 2207/20048; G06T 2207/20221; G06T 7/00; G06T 3/60; G16H 30/40
 See application file for complete search history.

(56) References Cited

OTHER PUBLICATIONS

Wu, J. and Xie, J., Jun. 2004. Zernike moment-based image registration scheme utilizing feedforward neural networks. In Fifth World Congress on Intelligent Control and Automation (IEEE Cat. No. 04EX788) (vol. 5, pp. 4046-4048). IEEE.*
Gao, X., Wang, Q., Li, X., Tao, D. and Zhang, K., 2011. Zernike-moment-based image super resolution. IEEE Transactions on Image Processing, 20(10), pp. 2738-2747.*
Ling Zhi-Gang et al., "A Robust Multi-Source Remote-Sensing Image Registration Method Based on Feature Matching", Acta Electronica Sinica, Dec. 2010, pp. 2892-2897.
Studholme et al., "An overlap invariant entropy measure of 3D medical image alignment", Pattern Recognition, Jan. 1999, pp. 71-86.
Wachinger et al., "Entropy and Laplacian images: Structural representations for multi-modal registration", Medical Image Analysis, Mar. 23, 2011, pp. 1-17.
Yang et al., "Two Phase Non-Rigid Multi-Modal Image Registration Using Weber Local Descriptor-Based Similarity Metrics and Normalized Mutual Information", Sensors, Jun. 13, 2013, pp. 7599-7617.
Heinrich, "MIND: Modality independent neighbourhood descriptor for multi-modal deformable registration", Medical Image Analysis, May 31, 2012, pp. 1423-1435.
"International Search Report (Form PCT/ISA/210)", dated Jan. 25, 2017, with English translation tereof, pp. 1-4.

* cited by examiner

REGISTRATION METHOD AND SYSTEM FOR NON-RIGID MULTI-MODAL MEDICAL IMAGE

CROSS-REFERENCE TO RELATED APPLICATION

This is a 371 application of the International PCT application serial no. PCT/CN2016/101547, filed on Oct. 9, 2016, which claims the priority benefits of China Application No. CN201610506619.9, filed on Jun. 30, 2016. The entirety of each of the above-mentioned patent applications is hereby incorporated by reference herein and made a part of this specification.

BACKGROUND OF THE INVENTION

Technical Field

The present invention belongs to the field of image registration in image processing and analysis, and more particularly relates to a registration method and system for a non-rigid multi-modal medical image.

Description of the Related Art

Medical imaging technologies constitute an important part of modern medicine and have revolutionary significance for the diagnosis and treatment of diseases. Despite the rapid advancement of such medical imaging technologies as ultrasound (US), computed tomography (CT), magnetic resonance imaging (MRI) and positron emission tomography (PET), they generally provide complementary information about the human body due to the different imaging principles. For example, US, CT and MRI could provide the anatomical information of the organs but fail to demonstrate their functional information. PET is good at demonstrating the metabolism information but it cannot provide morphological structures of organs clearly. To this end, doctors often need to fuse a variety of information from different modalities to improve the accuracy of medical imaging diagnosis. In this scenario, multi-modal image registration is essential for multi-modal image fusion.

The objective of image registration is to find correspondence between points that are present in the reference and floating images. In general, the image registration framework involves three main components including the deformation model, the similarity metric and the optimization method. However, the non-rigid multi-modal medical image registration has been a problem in the field of image registration due to intensity distortion, respiration and body motion in patients and some other factors.

At present, two approaches have been proposed to address the non-rigid multi-modal image registration problem. The first approach is a registration method based on mutual information. However, in this method, the local feature structures of the image are usually not considered, the calculation is time consuming and it is easy to get trapped in the local optimum, thereby resulting in inaccurate registration results. The second approach is to simplify the multi-modal image registration to mono-modal registration by image structure representation methods. For example, the image structure is represented by the entropy image, the Weber local descriptor (WLD), the modality independent neighborhood descriptor (MIND) and the like, and then the sum of squared differences (SSD) of the representation result is used as the registration metric for image registration. In the entropy image based registration method, an entropy value of each image patch is calculated by estimating the grey level probability density function of the image patches, thereby obtaining the entropy image of the entire image. Further, in the WLD-based registration method, Laplacian operation of the image is utilized to describe its local structural features. These two methods can effectively overcome the adverse influence of intensity differences between multi-modal images, but the entropy image and WLD based features are sensitive to image noise. Therefore, it is difficult to achieve accurate registration in the presence of image noise. In the MIND-based registration method, the image self-similarity is computed by the Euclidean distance between the image patches, and the sum of the self-similarities between different image patches is used to describe local structural features of the image. However, when evaluating the image self-similarity, this method only considers the translation invariance between the image patches while ignoring the possible rotation characteristic between the image patches. Therefore, in the presence of rotation characteristic between the image patches, it is difficult for this method to provide the accurate registration result.

SUMMARY OF THE INVENTION

In view of the above-described problems, the present invention provides a registration method and system for non-rigid multi-modal medical image based on image self-similarity, in which the self-similarity is computed on Zernike moments of image patches to construct the image feature descriptor, thereby achieving accurate non-rigid multi-modal medical image registration.

In order to achieve the above objective, according to an aspect of the present invention, there is provided a registration method for a non-rigid multi-modal medical image, comprising:

according to Zernike moments of order 0 and repetition 0 and Zernike moments of order 1 and repetition 1 of a reference image and a floating image, respectively obtaining local descriptors of the reference image and the floating image, and obtaining a registration image.

Preferably, the registration method specifically comprises:

step 1: obtaining a local descriptor $ZMLD^A(i)$ of the reference image $I^A(i)$ according to a Zernike moment $Z^A_{00}(i)$ of order 0 and repetition 0 and a Zernike moment $Z^A_{11}(i)$ of order 1 and repetition 1 of a pixel point i in the reference image $I^A(i)$, wherein i is an integer from 1 to M, and M represents the size of the reference image and the floating image;

step 2: obtaining a local descriptor $ZMLD^B(i)$ of the floating image $I^B(i)$ according to a Zernike moment $Z^B_{00}(i)$ of order 0 and repetition 0 and a Zernike moment $Z^B_{11}(i)$ of order 1 and repetition 1 of a pixel point i at the same position in the floating image $I^B(i)$; and step 3: establishing an objective function g(T) according to the local descriptors $ZMLD^A(i)$ and $ZMLD^B(i)$ of the reference image and the floating image; obtaining a transformation parameter according to the objective function, transforming the floating image according to the transformation parameter, and performing interpolation process on the transformed floating image, thereby obtaining the registration image.

Preferably, the step 2 comprises the following sub-steps:

step 2-1: obtaining a similarity distance $D^A_{00}(i)$ corresponding to the Zernike moment of order 0 and repetition 0 and a similarity distance $D^A_{11}(i)$ corresponding to the Zernike moment of order 1 and repetition 1 of the pixel point i to other pixel points in an image patch centered at the pixel point i in the reference image; simultaneously, obtaining a similarity distance $D^B_{00}(i)$ corresponding to the Zernike moment of order 0 and repetition 0 and a similarity distance $D^B_{11}(i)$ corresponding to the Zernike moment of order 1 and repetition 1 of the pixel point i to other pixel points in an image patch centered at the pixel point i in the floating image; and step 2-2: obtaining the local descriptor $ZMLD^A(i)$ of the reference image and the local descriptor $ZMLD^B(i)$ of the floating image, $$ZMLD^A(i) = \exp\left(-\frac{D^A_{00}(i)}{h^A_{00}(i)} - \frac{D^A_{11}(i)}{h^A_{11}(i)}\right),$$

$$ZMLD^B(i) = \exp\left(-\frac{D^B_{00}(i)}{h^B_{00}(i)} - \frac{D^B_{11}(i)}{h^B_{11}(i)}\right),$$

wherein $h^A_{00}(i)$, $h^A_{11}(i)$, $h^B_{00}(i)$ and $h^B_{00}(i)$ are decay parameters.

Preferably, the image patches in the step 2-1 all have a side length of 3, and in the step 2-2, $$h^A_{00}(i) = \{\sigma^A_{00}(i) + c_1 \cdot 1.4826 MED[|\sigma^A_{00}(i) - MED(|\sigma^A_{00}(i)|)|]\}^2,$$

$$\sigma^A_{00}(i) = c_2 \frac{|8|Z^A_{00}(i)| - \sum |Z^A_{00}(j)||}{\sqrt{72}},$$

$$h^A_{11}(i) = \{\sigma^A_{11}(i) + c_1 \cdot 1.4826 MED[|\sigma^A_{11}(i) - MED(|\sigma^A_{11}(i)|)|]\}^2,$$

$$\sigma^A_{11}(i) = c_2 \frac{|8|Z^A_{11}(i)| - \sum |Z^A_{11}(j)||}{\sqrt{72}},$$

$$h^B_{00}(i) = \{\sigma^B_{00}(i) + c_1 \cdot 1.4826 MED[|\sigma^B_{00}(i) - MED(|\sigma^B_{00}(i)|)|]\}^2,$$

$$\sigma^B_{00}(i) = c_2 \frac{|8|Z^B_{00}(i)| - \sum |Z^B_{00}(j)||}{\sqrt{72}},$$

$$h^B_{11}(i) = \{\sigma^B_{11}(i) + c_1 \cdot 1.4826 MED[|\sigma^B_{11}(i) - MED(|\sigma^B_{11}(i)|)|]\}^2,$$

$$\sigma^B_{11}(i) = c_2 \frac{|8|Z^B_{11}(i)| - \sum |Z^B_{11}(j)||}{\sqrt{72}},$$

wherein MED(•) represents the median operator, $c_1$ and $c_2$ are constants of 0.5-1, and j is any pixel point in an image patch centered at the pixel point i.

Preferably, the step 3 specifically comprises the following sub-steps:

step 3-1: establishing an objective function $g(T_\tau)=SSD+\alpha R(T_\tau)$, wherein SSD represents the sum of squared differences between the local descriptors $ZMLD^A(i)$ and $ZMLD^B(i)$, $\alpha$ ($0<\alpha<1$) is a constant, $R(T_\tau)$ represents a regularization term, and the number of iterations $\tau$ is initially set to be 1; iteratively solving the objective function $g(T_\tau)$ to obtain a transformation parameter $T_\tau$;

step 3-2: transforming the local descriptor $ZMLD^B(i)$ of the floating image according to the transformation parameter $T_\tau$, performing interpolation process on the transformed local descriptor, and updating the original local descriptor $ZMLD^B(i)$ with the local descriptor subjected to the interpolation process, $\tau=\tau+1$; iteratively solving the objective function $g(T_\tau)$ to obtain a transform parameter $T_\tau$;

step 3-3: if the number of iterations r is greater than or equal to a threshold $\xi$ of the number of iterations and $g(T_\tau) \geq g(T_{\tau-1})$, transforming the floating image according to the transformation parameter $T_\tau$, and performing interpolation process on the transformed floating image to obtain the registration image; otherwise, returning to the step 3-2.

Preferably, the iteration solution is performed by the limited memory Broyden-Fletcher-Goldfarb-Shanno method (L-BFGS method) or the gradient descent method, the transformation is performed by using the B-spline Free-form Deformation model, and the interpolation process is performed by the bilinear interpolation method or the B-spline interpolation method.

Preferably, the similarity metric SSD of the local descriptors $ZMLD^A(i)$ and $ZMLD^B(i)$ in the step 3-1 is expressed as:

$$SSD = \frac{\sum_{i=1}^{M}[ZMLD^A(i) - ZMLD^B(i)]^2}{M}.$$

Preferably, the transformation parameter T is a third-order B-spline function.

Preferably, a threshold $\xi$ of the number of iterations meets the following condition:

$$50 \geq \xi \geq 20.$$

According to another aspect of the present invention, there is further provided a registration system for a non-rigid multi-modal medical image, and the registration system comprises a first Zernike moment module, a first descriptor module, a second Zernike moment module, a second descriptor module and a registration module;

the first Zernike moment module is configured to obtain Zernike moments of order 0 and repetition 0 and Zernike moments of order 1 and repetition 1 of a reference image and output them to the first descriptor module, and the first descriptor module is configured to obtain local descriptors of the reference image and output them to the registration module; the second Zernike moment module is configured to obtain Zernike moments of order 0 and repetition 0 and Zernike moments of order 1 and repetition 1 of a floating image and output them to the second descriptor module, and the second descriptor module is configured to obtain local descriptors of the floating image and output them to the registration module; the registration module is configured to obtain a registration image.

Preferably, the registration module includes a solving unit and a determining unit. The solving unit is configured to construct an objective function according to the local descriptors of the reference image and the floating image, obtain a transformation parameter and output the transformation parameter to the determining unit. The determining unit is configured to determine whether the objective function meets an iteration stopping criterion. If it is not, the local descriptor of the floating image is transformed according to the transformation parameter, interpolation process is performed on the transformed local descriptor, the original local descriptor of the floating image is updated with the local descriptor of the floating image subjected to the interpolation process. Otherwise, the floating image is transformed according to the transformation parameter and interpolation process is performed on the floating image to obtain the registration image.

Compared with the prior art, the above technical solution proposed by the present invention respectively extracts intensity information and edge feature information by Zernike moments of order 0 and repetition 0 and Zernike moments of order 1 and repetition 1, thereby constructing the local descriptors ZMLD, so that the local structural information of the complex medical image can be represented in the presence of image noise and rotation between image features, which provides an effective basis for the accurate evaluation of the similarity between the multimodal images.

DETAILED DESCRIPTION OF THE EMBODIMENTS

For clear understanding of the objectives, features and advantages of the present invention, detailed description of the present invention will be given below in conjunction with accompanying drawings and specific embodiments. It should be noted that the embodiments described herein are only meant to explain the present invention, and not to limit the scope of the present invention. Furthermore, the technical features related to the embodiments of the invention described below can be mutually combined if they are not found to be mutually exclusive.

Figure 1:
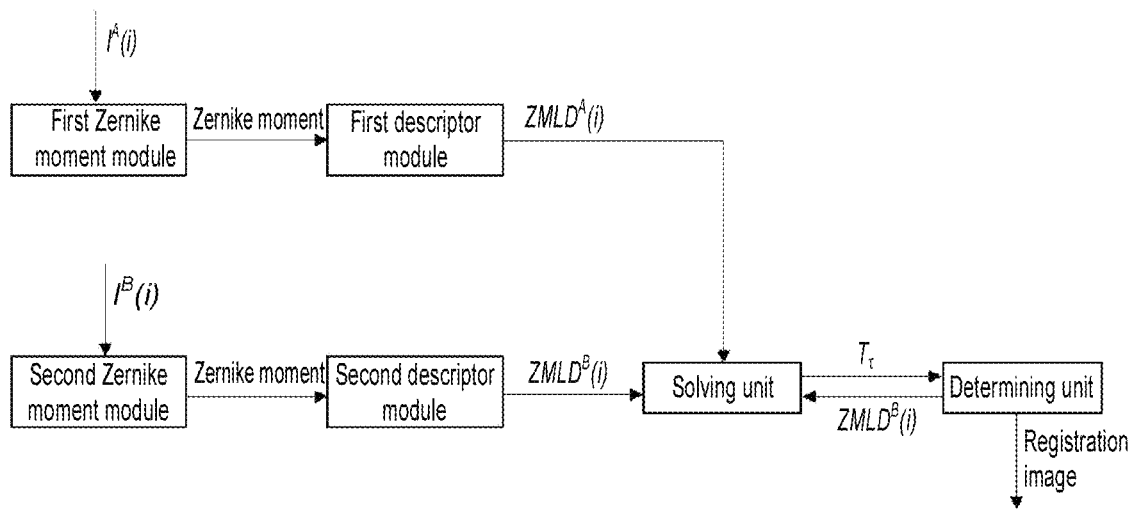
FIG. 1 is a schematic structural diagram of a registration system for a non-rigid multi-modal medical image according to the present invention.
Figure 2:
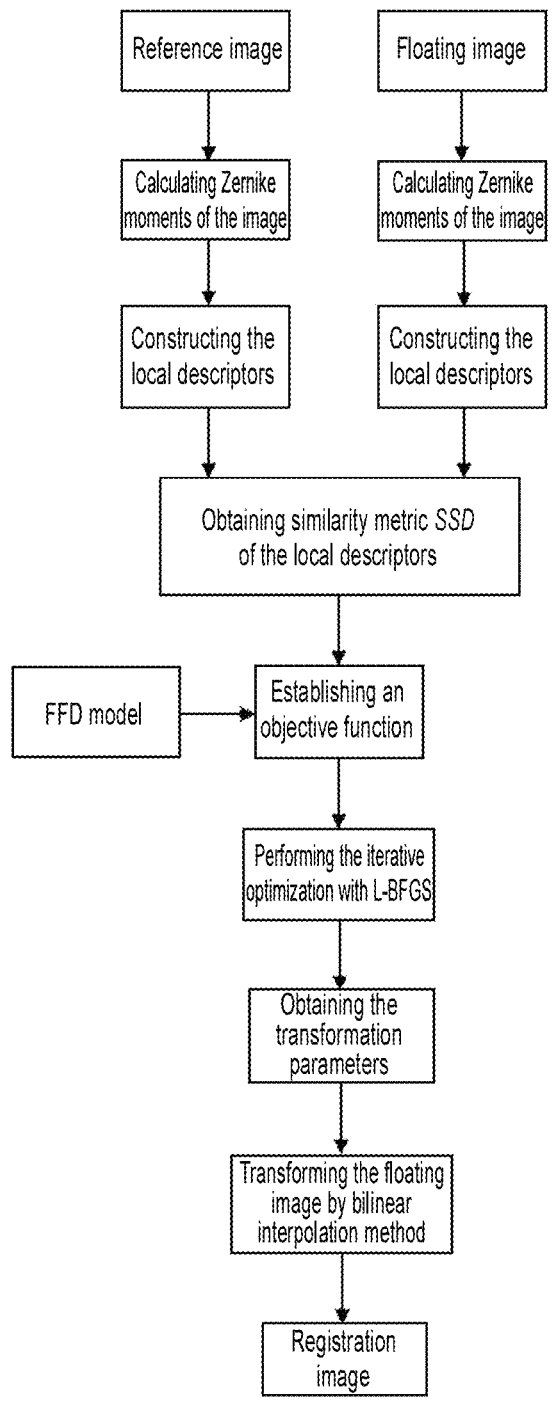
FIG. 2 is a flow chat of a registration method for a non-rigid multi-modal medical image according to Embodiment 1 of the present invention.
Figure 3A:
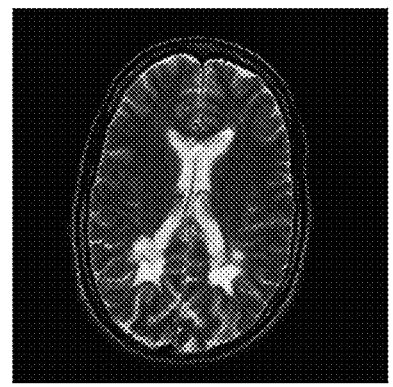
FIG. 3a is a reference T2 image used in Embodiment 1 and Comparative Examples 2-4 of the present invention.
Figure 3B:
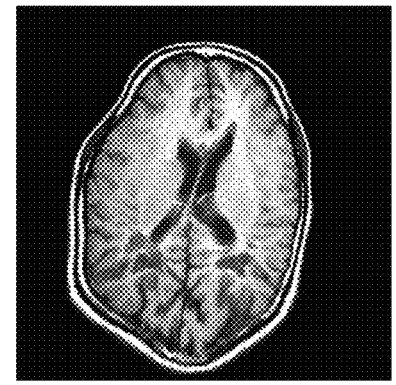
FIG. 3b is a floating T1 image used in Embodiment 1 and Comparative Examples 2-4 of the present invention.
Figure 3C:
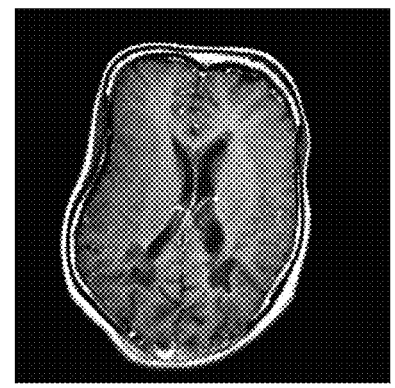
FIG. 3c is a floating Gad image used in Embodiment 1 and Comparative Examples 2-4 of the present invention.
Figure 3D:
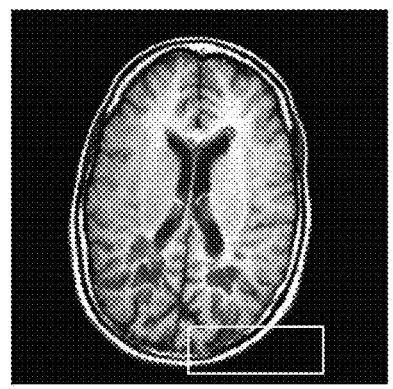
FIG. 3d is a registration T1-T2 image obtained by the method according to Embodiment 1 of the present invention.
Figure 3E:
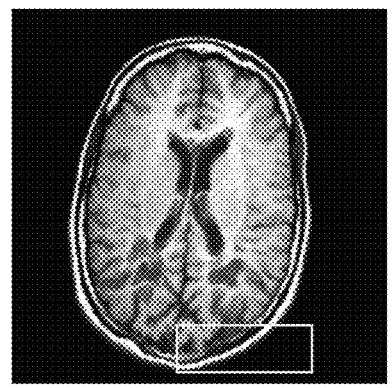
FIG. 3e is a registration T1-T2 image obtained by the method according to Comparative Example 4 of the present invention.
Figure 3F:
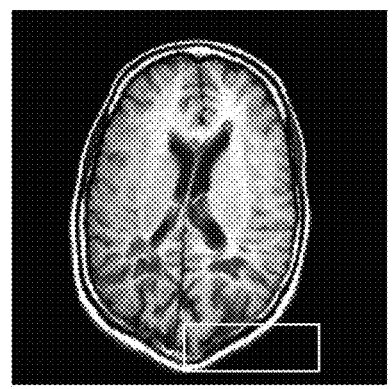
FIG. 3f is a registration T1-T2 image obtained by the method according to Comparative Example 3 of the present invention.
Figure 3G:
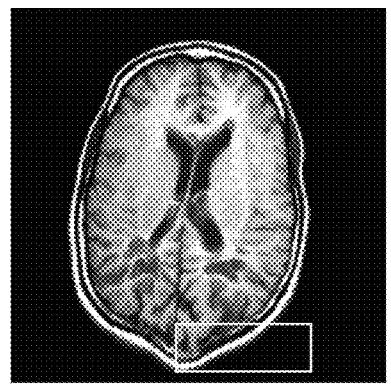
FIG. 3g is a registration T1-T2 image obtained by the method according to Comparative Example 2 of the present invention.
Figure 3H:
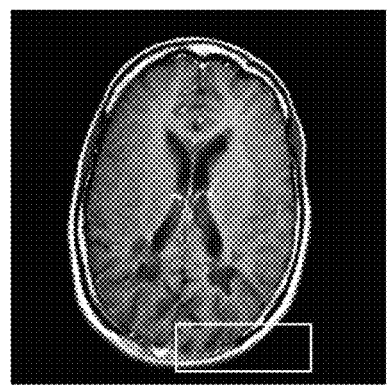
FIG. 3h is a registration Gad-T2 image obtained by the method according to Embodiment 1 of the present invention.
Figure 3I:
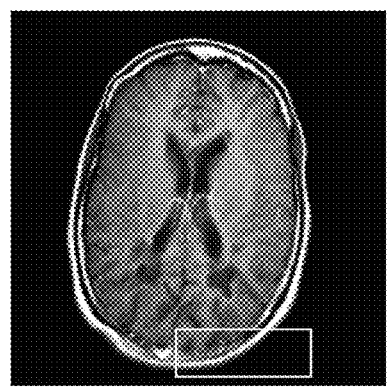
FIG. 3i is a registration Gad-T2 image obtained by the method according to Comparative Example 4 of the present invention.
Figure 3J:
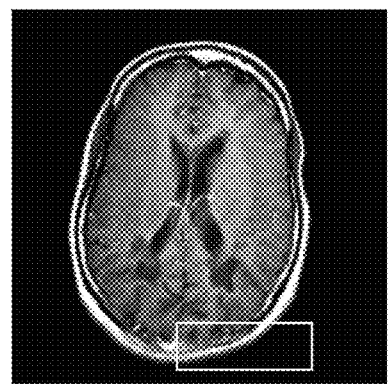
FIG. 3j is a registration Gad-T2 image obtained by the method according to Comparative Example 3 of the present invention.
Figure 3K:
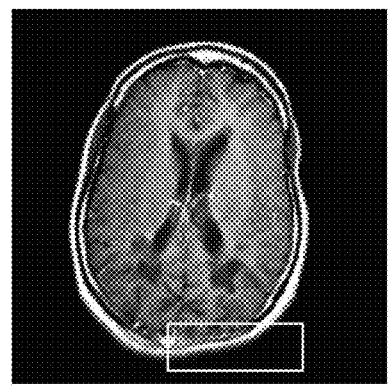
FIG. 3k is a registration Gad-T2 image obtained by the method according to Comparative Example 2 of the present invention.

The present invention provides a registration system for a non-rigid multi-modal medical image, which comprises a first Zernike moment module, a first descriptor module, a second Zernike moment module, a second descriptor module and a registration module, in which the registration module further includes a solving unit and a determining unit as shown in FIG. 1.

An output end of the first Zernike moment module is connected to an input end of the first descriptor module, an output end of the first descriptor module is connected to a first input end of the solving unit, an output end of the second Zernike moment module is connected to an input end of the second descriptor module, and an output end of the second descriptor module is connected to a second input end of the solving unit; an output end of the solving unit is connected to an input end of the determining unit, and an output end of the determining unit is connected to an input end of the second Zernike moment module.

The first Zernike moment module is configured to obtain and output Zernike moments $Z^A_{00}(i)$ of order 0 and repetition 0 and Zernike moments $Z^A_{11}(i)$ of order 1 and repetition 1 of a reference image $A(i)$, and the first descriptor module is configured to obtain and output local descriptors $ZMLD^A(i)$ of the reference image; the second Zernike moment module is configured to obtain and output Zernike moments $Z^B_{00}(i)$ of order 0 and repetition 0 and Zernike moments $Z^B_{11}(i)$ of order 1 and repetition 1 of a floating image $I^B(i)$, the second descriptor module is configured to obtain and output local descriptors $ZMLD^B(i)$ of the floating image, the solving unit is configured to construct an objective function $g(T_\tau)$ according to the local descriptors of the reference image and the floating image and obtain a transformation parameter $T_\tau$, and the determining unit is configured to determine whether the objective function meets an iteration stopping criterion. If it is not, the local descriptor of the floating image is transformed according to the transformation parameter, interpolation process is performed on the transformed local descriptor, the original local descriptor of the floating image is updated with the local descriptor of the floating image subjected to interpolation process; Otherwise, the floating image is transformed according to the transformation parameter and interpolation process is performed on the floating image to obtain the registration image.

Specifically, registration of the non-rigid multi-modal medical image by the registration system includes the following steps:

Step 1: obtaining a local descriptor $ZMLD^A(i)$ of the reference image $I^A(i)$ according to the Zernike moment $Z^A_{00}(i)$ of order 0 and repetition 0 and the Zernike moment $Z^A_{11}(i)$ of order 1 and repetition 1 of the pixel point i in the reference image $I^A(i)$, wherein i is an integer from 1 to M, and M is the size of the reference image and the floating image (that is, when the images have a length of X and a width of Y, M=X×Y).

Step 1-1: calculating the Zernike moment by the following formulas:

$$Z_{nm} = \frac{n+1}{\lambda_N} \sum_{x=0}^{N-1} \sum_{y=0}^{N-1} R_{nm}(\rho_{xy}) e^{-jm\theta_{xy}} f(x, y) \quad (1)$$

-continued $$R_{nm}(\rho) = \sum_{s=0}^{(n-|m|)/2} (-1)^s \frac{(n-s)!}{s!(((n+|m|)/2)-s)!(((n-|m|)/2-s)!} \rho^{n-2s} \quad (2)$$

$$\rho_{xy} = \frac{\sqrt{(2x-N+1)^2 + (2y-N+1)^2}}{N}, \theta_{xy} = \tan^{-1}\left(\frac{N-1-2y}{2x-N+1}\right)$$

wherein N represents the side length of the first image patch centered at the pixel point i (N is usually an odd number between 3 and 11 and can be selected by taking into comprehensive consideration of the complexity, calculation efficiency and image registration accuracy; when the image complexity is high, the registration accuracy requirement is not high or a high calculation efficiency is required, a smaller value such as 3 or 5 may be taken, otherwise, a larger value may be taken); $f(x,y)$ represents an image function of the first image patch centered at the pixel point i, and $\theta$ and $\rho$ respectively represent a polar angle and a polar axis of the pixel point in the image function $f(x,y)$ (when the pixel point i is located at the edges of the reference image and the floating image, an image function value of a pixel point in the first image patch which exceeds the range of the original reference image and floating image is filled with the image function value of the pixel adjacent thereto); x and y represent coordinates of any pixel in the image function $f(x,y)$, relative to the center point i of the first image patch, in the first image patch; $j=\sqrt{-1}$, $\lambda_N$ is a normalization factor, $\lambda_N=N^2$; m represents the repetition of the Zernike moment, n represents the order of the Zernike moment, and s=0–(n–|m|)/2 (in the present invention, s=0, $R_{00}(\rho)=1$ and $R_{11}(\rho)=\rho$ since n=m=1 or n=m=0).

When n=m=0, Zernike moments of order 0 and repetition 0 of the image are obtained, an when n=m=1, Zernike moments of order 1 and repetition 1 of the image are obtained; thus, the Zernike moment $Z^A_{00}(i)$ of order 0 and repetition 0 and the Zernike moment $Z^A_{11}(i)$ of order 1 and repetition 1 of the pixel point i in the reference image can be obtained by the above formulas, and meanwhile, the Zernike moment $Z^B_{00}(i)$ of order 0 and repetition 0 and the Zernike moment $Z^B_{11}(i)$ of order 1 and repetition 1 of the pixel point i at the same position in the floating image are obtained.

Step 1-2: in the reference image, obtaining similarity distances $D^A_{00}(i)$ and $D^A_{11}(i)$ of the pixel point i to other pixel points in the second image patch centered at the pixel point i, the calculation formula being as follows:

$$D_{nm}(i) = \frac{1}{(|r|)^2 - 1} \sum_{j \in r} (|Z_{nm}(i)| - |Z_{nm}(j)|)^2,$$

wherein |r| represent the side length of the second image patch, which is usually an odd number larger than or equal to 3,j is any pixel point other than the pixel point i in the second image block, and $|Z_{nm}(i)|$ and $|Z_{nm}(j)|$ are modulus of the Zernike moments of order n and repetition m of the pixel point i and the pixel point j, respectively; when the pixel point i is located at the edge of the reference image, the modulus of the Zernike moment of a pixel point in the second image patch that exceeds the range of the reference image is filled with the modulus of the Zernike moment of the pixel point adjacent thereto; thus, $D^A_{00}(i)$, $D^A_{11}(i)$, $D^B_{00}(i)$ and $D^B_{11}(i)$ can be obtained.

Steps 1-3: obtaining the local descriptors ZMLD, the formula being as follows:

$$ZMLD(i) = \exp\left(-\frac{D_{00}(i)}{h_{00}(i)} - \frac{D_{11}(i)}{h_{11}(i)}\right),$$

wherein $h_{00}(i,r)$ and $h_{11}(i,r)$ are decay parameters, and the calculation formula thereof is as follows:

$$h_{nm}(i) = [\sigma_{nm}^l(i) + \sigma_{nm}^g(i)]^2, \ n=m=0 \text{ or } n=m=1,$$

for example, when |r|=3, $\sigma_{nm}^l(i)$ and $\sigma_{nm}^g(i)$ are respectively expressed as:

$$\sigma_{nm}^g(i) = c_1 \cdot 1.4826 MED[|\sigma_{nm}^l(i) - MED(|\sigma_{nm}^l(i)|)|],$$

$$\sigma_{nm}^l(i) = c_2 \varepsilon_i = c_2 \frac{\left|8|Z_{nm}(i)| - \sum_{j \in r} |Z_{nm}(j)|\right|}{\sqrt{72}},$$

wherein MED(•) represents the median operator, and $c_1$ and $c_2$ are adjustment coefficients with $0.5 < c_1 \leq 1$ and $0.5 < c_2 \leq 1$.

According to the above formulas, local descriptors $ZMLD^A(i)$ of the reference image can be respectively obtained.

Step 2: by the same calculation method as in the step 1, obtaining a local descriptor $ZMLD^B(i)$ of the floating image according to the Zernike moment $Z^B_{00}(i)$ of order 0 and repetition 0 and the Zernike moment $Z^B_{11}(i)$ of order 1 and repetition 1 of the pixel point i at the same position in the floating image.

Step 3, establishing an objective function according to the local descriptors $ZMLD^A(i)$ and $ZMLD^B(i)$, and finally achieving registration of the reference image and the floating image; taking an example of establishing an objective function with the B-spline Free-form Deformation (FFD) model as the transformation model, the registration process is described, the registration process specifically comprising the following sub-steps:

Step 3-1: establishing an objective function $g(T_\tau)=SSD+\alpha R(T_\tau)$, in which the smaller the value of $g(T_\tau)$, the more similar the floating image is to the reference image, SSD represents the similarity metric between the local descriptors $ZMLD^A(i)$ and $ZMLD^B(i)$, $$SSD = \frac{\sum_{i=1}^{M} [ZMLD^A(i) - ZMLD^B(i)]^2}{M},$$

wherein $\alpha$ (0<$\alpha$<1) represents a weighting parameter, $T_\tau$ is a third-order B-spline function related to the coordinates (x, y) of the pixel point i, which represents a transformation parameter for transforming the floating image into a registration image; $R(T_\tau)$ is a regularization term, and the calculation formula thereof is as follow:

$$R(T_\tau) = \frac{1}{X \times Y} \sum_{x=1}^{X} \sum_{y=1}^{Y} \left[\left(\frac{\partial^2 T_\tau(x,y)}{\partial x^2}\right)^2 + 2\left(\frac{\partial^2 T_\tau(x,y)}{\partial xy}\right)^2 + \left(\frac{\partial^2 T_\tau(x,y)}{\partial y^2}\right)^2\right],$$

wherein, x and y respectively represents the horizontal coordinate and vertical coordinate of the pixel point i in the floating image, and X and Y respectively represent the length and width of the floating image, then X×Y=M; and the number of iterations τ is initially set to be 1; the objective function $g(T_\tau)$ is solved iteratively by the limited memory Broyden-Fletcher-Goldfarb-Shanno method or the gradient descent method to obtain a transform parameter $T_\tau(x,y)$.

Step 3-2: transforming the local descriptor $ZMLD^B(i)$ of the floating image according to the transformation parameter $T_\tau(x,y)$, performing interpolation process on the transformed local descriptor by the bilinear interpolation method or the B-spline interpolation method, and updating the original local descriptor $ZMLD^B(i)$ with the local descriptor subjected to the interpolation process, τ=τ+1; iteratively solving the objective function $g(T_\tau)$ to obtain a transform parameter $T_\tau$.

Step 3-3, if the number of iterations r is greater than or equal to a threshold ξ (generally, 50≥ξ≥20) of the number of iterations and $g(T_\tau) \geq g(T_{\tau-1})$, transforming the floating image according to the transformation parameter $T_\tau(x,y)$, and performing interpolation process on the transformed floating image by the bilinear interpolation method or the B-spline interpolation method to obtain the registration image $I'^B(i)$, thereby completing image registration; otherwise; returning to the step 3-2.

Embodiment 1

The present invention provides a registration method for a non-rigid multi-modal medical image, and as shown in FIG. 1, the method comprises the following steps:

Step 1: calculating Zernike moments of order 0 and repetition 0 and Zernike moments of order 1 and repetition 1 of the first image patch centered at each pixel point i in the reference image and the floating image according to the formulas (1) and (2); finally obtaining moment features $Z^A_{00}(i)$ and $Z^A_{11}(i)$ of the reference image $I_A$ and moment features $Z^B_{00}(i)$ and $Z^B_{11}(i)$ of the floating image $I_B$.

Step 2: calculating Zernike moment based local descriptors (referred to as ZMLD) according to the moment features.

Step 2-1: based on the image self-similarity, calculating similarity distances $D^A_{00}(i)$, $D^A_{11}(i)$, $D^B_{00}(i)$ and $D^B_{11}(i)$ of the pixel point i to other pixel points in the second image patch centered at the pixel point i in the reference image and the floating image, the formula being as follow:

$$D_{nm}(i,r) = \frac{1}{(|r|)^2 - 1} \sum_{j \in r} (|Z_{nm}(i)| - |Z_{nm}(j)|)^2,$$

n=m=0 or n=m=1
wherein $|Z_{nm}(i)|$ and $|Z_{nm}(j)|$ are modulus of Zernike moments of order n and repetition m of the pixel point i and the pixel point j, respectively; |r| represent the side length of the second image patch, and when |r|=3, a high registration accuracy can be ensured; in the present embodiment, when |r|>3, the registration accuracy is not increased and the computational efficiency decreases, and when |r|<3, the registration accuracy is obviously affected; j is any pixel point other than the pixel point i in the second image patch.

Step 2-2: obtaining local descriptors ZMLD, the calculation formula being as follows:

$$ZMLD(i) = \exp\left(-\frac{D_{00}(i)}{h_{00}(i)} - \frac{D_{11}(i)}{h_{11}(i)}\right),$$

wherein $h_{00}(i,r)$ and $h_{11}(i,r)$ are decay factors, and the calculation formula thereof is as follows:

$$h_{nm}(i) = [\sigma_{nm}^l(i) + \sigma_{nm}^g(i)]^2, \; n=m=0 \text{ or } n=m=1$$

Since |r|=3 in the present embodiment, $\sigma_{nm}^l(i)$ and $\sigma_{nm}^g(i)$ are respectively expressed as below:

$$\sigma_{nm}^g(i) = c_1 \cdot 1.4826 MED[|\sigma_{nm}^l(i) - MED(|\sigma_{nm}^l(i)|)|],$$

$$\sigma_{nm}^l(i) = c_2 \varepsilon_i = c_2 \frac{\left|8|Z_{nm}(i)| - \sum_{j \in r} |Z_{nm}(j)|\right|}{\sqrt{72}},$$

wherein MED(•) represents the median operator, and $c_1$ and $c_2$ represent adjustment coefficients (in present embodiment, $c_1 = c_2 = 0.8$).

According to the above formulas, local descriptors $ZMLD^A(i)$ of the reference image and local descriptors $ZMLD^B(i)$ of the floating image can be respectively obtained.

Step 3-1: establishing an objective function $g(T_\tau) = SSD + \alpha R(T_\tau)$ by taking the B-spline Free-form Deformation (FFD) model as the transformation model, in which SSD represents the similarity metric between the local descriptors $ZMLD^A(i)$ and $ZMLD^B(i)$, $$SSD = \frac{\sum_{i=1}^{M} [ZMLD^A(i) - ZMLD^B(i)]^2}{M},$$

wherein M represents the image size (in the present embodiment, since both the length X and the width Y of the reference image and the floating image are 256, M=X× Y=256×256); α represents a weighting parameter (α=0.015), T represents a transformation parameter for transforming the floating image into a registration image; and R(T) represents a regularization term, the calculation formula thereof being as follow:

$$R(T_\tau) = \frac{1}{X \times Y} \sum_{x=1}^{X} \sum_{y=1}^{Y} \left[\left(\frac{\partial^2 T_\tau(x,y)}{\partial x^2}\right)^2 + 2\left(\frac{\partial^2 T_\tau(x,y)}{\partial xy}\right)^2 + \left(\frac{\partial^2 T_\tau(x,y)}{\partial y^2}\right)^2\right],$$

Step 3-2: iteratively solving the objective function g(T) with the L-BFGS method with the aim of minimizing the value of g(T), and when g(T) gets the minimum value and the number of iterations is greater than or equal to a threshold ξ of the number of iterations, stopping the iteration to obtain a transformation parameter T.

Step 3-3: transforming the floating image by using the transformation parameter T obtained in the step 3-2, and performing interpolation process by the bilinear interpolation method to obtain a registration image corresponding to the floating image, thereby completing image registration.

Comparative Example 1

The registration was carried out according to the NMI method in the prior art (Pattern Recognit. 32(1) (1999) 71-86.).

Comparative Example 2

The registration was carried out according to the ESSD method in the prior art (Med. Image Anal. 16(1) (2012) 1-17.), in which the specific parameters are as follows: selecting 7×7 image patches, and calculating the entropy corresponding to the image patches by using the Gaussian weight, local normalization method and Parzen-window estimation, thereby obtaining the ESSD corresponding to the entire image.

Comparative Example 3

The registration was carried out according to the WLD method in the prior art (Sensors 13(6) (2013) 7599-7613), in which the specific parameters are as follows: the radius for WLD calculation is R=1 and R=2, the patch size for the similarity metric is 7×7, and the weight term γ=0.01.

Comparative Example 4

The registration was carried out according to the MIND method in the prior art (Med. Image Anal. 16(7) (2012) 1423-1435), in which the specific parameters are as follow: the patch size is 3×3.

Analysis of Results

In order to further embody the advantages of the present invention, comparison of the registration accuracy of Embodiment 1 and Comparative Examples 1-4 was made. The registration accuracy is evaluated using the target registration error (TRE), wherein TRE is defined as:

$$TRE = \frac{\|T_s(R) - T_c(R)\|_2}{|R|}$$

wherein $T_s$ represents the random deformation and is also the gold standard for evaluation, $T_c$ represents the deformation obtained by the registration method, and R represents the number of pixels used for image registration performance evaluation.

The simulated MR image was used for the registration accuracy test. The simulated T1, T2 and PD weighted MR images used in Example 1 were taken from the BrainWeb database. Table 1 lists the standard deviation and mean of the TRE obtained by all evaluated methods. It can be seen from Table 1 that when registration is performed on different MR images, the TRE provided in Embodiment 1 has lower mean and standard deviation than other methods, which indicates that the method proposed by the present invention has the highest registration accuracy among all the compared methods.

TABLE 1

Comparison of TREs (mm) for all evaluated methods performed on T1-T2, PD-T2 and T1-PD images

| | Registration method | | | | | |
| --- | --- | --- | --- | --- | --- | --- |
| | T1-T2 | | PD-T2 | | T1-PD | |
| | Mean | Standard deviation | Mean | Standard deviation | Mean | Standard deviation |
| No registration | 4.35 | 3.32 | 4.50 | 3.52 | 4.49 | 2.27 |
| Comparative Example 1 | 1.81 | 2.33 | 1.95 | 1.98 | 2.12 | 1.94 |
| Comparative Example 2 | 1.53 | 1.41 | 1.92 | 1.66 | 1.97 | 2.19 |
| Comparative Example 3 | 1.46 | 1.53 | 0.97 | 1.10 | 1.63 | 1.35 |
| Comparative Example 4 | 1.02 | 1.16 | 0.96 | 0.99 | 0.97 | 1.06 |
| Embodiment 1 | 0.65 | 0.58 | 0.73 | 0.62 | 0.89 | 0.95 |

To more intuitively show the superiority of the present invention over the rest of the methods, visual comparisons of the registration images corresponding to Embodiment 1 and Comparative Examples 2-4 were provided, as shown in FIG. 3. FIG. 3a shows a reference T2 image, FIG. 3b shows a floating T1 image, FIG. 3c shows a floating Gad image, FIG. 3d shows a registration T1-T2 image obtained by the method in Embodiment 1, FIG. 3e shows a registration T1-T2 image obtained by the method in Comparative Example 4, FIG. 3f shows a registration T1-T2 image obtained by the method in Comparative Example 3, FIG. 3g shows a registration T1-T2 image obtained by the method in Comparative Example 2, FIG. 3h shows a registration Gad-T2 image obtained by the method in Embodiment 1, FIG. 3i shows a registration Gad-T2 image obtained by the method in Comparative Example 4, FIG. 3j shows a registration Gad-T2 image obtained by the method in Comparative Example 3, and FIG. 3k shows a registration Gad-T2 image obtained by the method in Comparative Example 2.

By taking the partial contour of the image shown in the box as an example, for the registration T1-T2 image, the deformation of the lowermost portion of the contour cannot be effectively corrected in Comparative Examples 2-4. For the registration Gad-T2 image, Comparative Examples 3-4 do not provide a good correction for the deformation of the right portion of the box, while the above deformation can be effectively corrected in Embodiment 1. It can be seen that the registration image obtained in Embodiment 1 is more similar to the reference image than those obtained in Comparative Examples 2-4. The above visual comparison demonstrates that the local descriptor of the present invention has rotation invariance, and more accurate representation of the image, so that the present invention is superior in the non-rigid multi-mode medical image registration.

The registration accuracy of the listed methods is evaluated by using the T1, T2 and Grad weighted MR images in the Altas database, and Table 2 gives corresponding TRE results of the respective methods. The results in the Table 2 indicate that the method proposed in the present invention can provide a lower TRE than other methods, and thus has a higher registration accuracy.

TABLE 2

Comparison of TREs (mm) for all evaluated methods performed on T1-T2, Gad-T2 and Gad-T1 images

| Registration method | | | | | | |
|---|---|---|---|---|---|---|
| | T1-T2 | | Gad-T2 | | Gad-T1 | |
| | Mean | Standard deviation | Mean | Standard deviation | Mean | Standard deviation |
| No registration | 5.21 | 2.70 | 4.86 | 2.41 | 6.50 | 2.15 |
| Comparative Example 1 | 3.38 | 2.15 | 3.17 | 1.94 | 3.86 | 1.98 |
| Comparative Example 2 | 2.83 | 1.89 | 3.05 | 1.76 | 3.18 | 1.82 |
| Comparative Example 3 | 2.61 | 1.77 | 2.74 | 1.62 | 2.99 | 1.66 |
| Comparative Example 4 | 2.45 | 1.58 | 2.34 | 1.56 | 2.60 | 1.53 |
| Embodiment 1 | 2.12 | 1.40 | 2.19 | 1.24 | 2.44 | 1.37 |

Figure 4A:
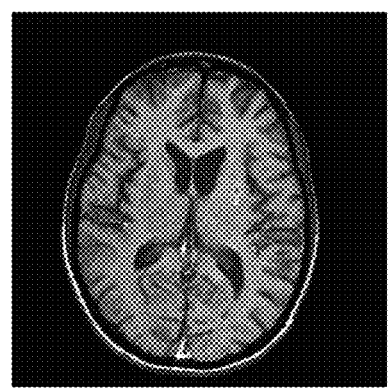
FIG. 4a is a reference T1-weighted MR image used in Embodiment 1 and Comparative Examples 2-4 of the present invention.
Figure 4B:
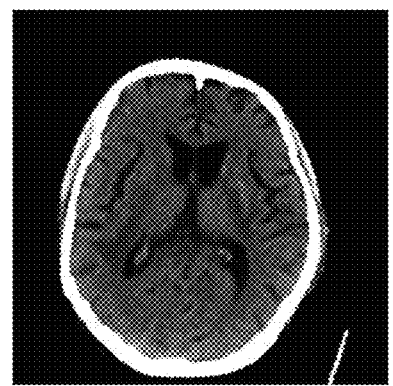
FIG. 4b is a floating image CT used in Embodiment 1 and Comparative Examples 2-4 of the present invention.
Figure 4C:
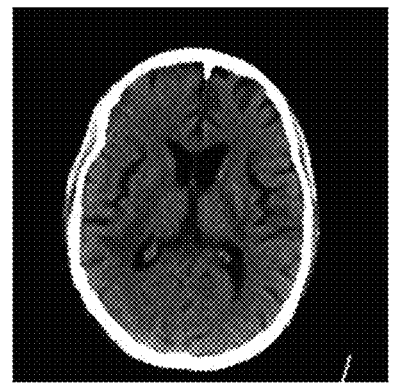
FIG. 4c is a registration image obtained by the method according to Embodiment 1 of the present invention.
Figure 4D:
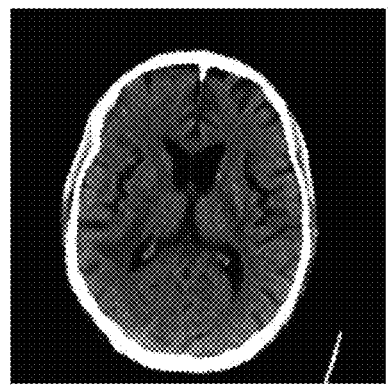
FIG. 4d is a registration image obtained by the method according to Comparative Example 4 of the present invention.
Figure 4E:
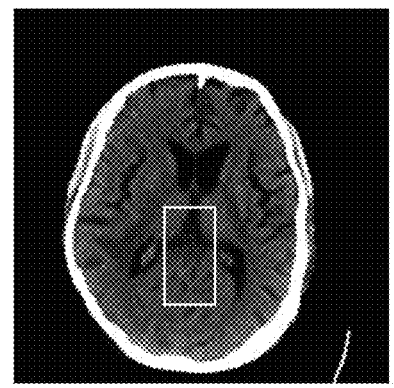
FIG. 4e is a registration image obtained by the method according to Comparative Example 3 of the present invention.
Figure 4F:
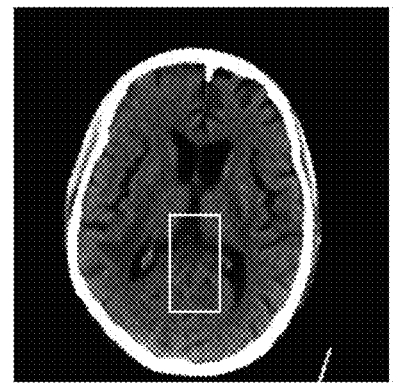
FIG. 4f is a registration image obtained by the method according to Comparative Example 2 of the present invention.

For the comparison of the registration accuracy between CT and MR images, five kinds of random deformation processing on the floating CT images were performed. FIG. 4 shows registration results of real CT and MR images by the methods of Embodiment 1 and Comparative Examples 2-4. FIG. 4a shows a reference T1 weighted MR image, FIG. 4b shows a floating CT image, FIG. 4c shows a registration image obtained by the method of Embodiment 1, FIG. 4d shows a registration image obtained by the method of Comparative Example 4, FIG. 4e shows a registration image obtained by the method of Comparative Example 3, and FIG. 4f shows a registration image obtained by the method of Comparative Example 2. It can be seen that it is difficult for the methods in Comparative Examples 3-4 to effectively correct the deformation of the contour in the box, and the outermost contour of the registration image provided in Comparative Example 2 is partially distorted, while the method in Embodiment 1 can provide a more satisfactory registration image. Table 3 shows the average value of the TRE in registration of each group of real CT image and MR image, in which images in Group 5 are the real CT image and MR image used in FIG. 4.

TABLE 3

Comparison of TREs (mm) for all evaluated methods performed on CT-MR images

| | TRE | | | | |
|---|---|---|---|---|---|
| Registration method | Group 1 | Group 2 | Group 3 | Group 4 | Group 5 |
| No registration | 3.81 | 5.74 | 3.94 | 4.49 | 5.67 |
| Comparative Example 1 | 3.19 | 4.29 | 3.48 | 3.99 | 4.64 |
| Comparative Example 2 | 2.92 | 3.87 | 3.24 | 3.41 | 4.06 |
| Comparative Example 3 | 2.81 | 3.66 | 2.92 | 3.36 | 3.93 |
| Comparative Example 4 | 2.80 | 3.06 | 2.97 | 2.63 | 3.09 |
| Embodiment 1 | 2.64 | 2.50 | 2.89 | 2.52 | 2.75 |

It can be seen from Table 3 that the method of the present invention can achieve a lower TRE in registration of the CT-MR images of Groups 1-5 than other registration methods, which indicates that the method of the present invention can achieve higher registration accuracy in registration of the CT-MR images than the algorithms in the Comparative Examples.

It should be readily understood to those skilled in the art that the above description is only preferred embodiments of the present invention, and does not limit the scope of the present invention. Any change, equivalent substitution and modification made without departing from the spirit and scope of the present invention should be included within the scope of the protection of the present invention.

What is claimed is:

1. A registration method for a non-rigid multi-modal medical image, comprising:
according to Zernike moments of order 0 and repetition 0 and Zernike moments of order 1 and repetition 1 of a reference image and a floating image, respectively obtaining a local descriptor of the reference image and a local descriptor of the floating image, and obtaining a registration image, wherein the method comprises the following steps:

step 1: obtaining the local descriptor $ZMLD^A(i)$ of the reference image $I^A(i)$ according to a Zernike moment $Z^A_{00}(i)$ of order 0 and repetition 0 and a Zernike moment $Z^A_{11}(i)$ of order 1 and repetition 1 of a pixel point i in the reference image $I^A(i)$, wherein i is an integer from 1 to M, and M represents the size of the reference image and the floating image;

step 2: obtaining the local descriptor $ZMLD^B(i)$ of the floating image $I^B(i)$ according to a Zernike moment $Z^B_{00}(i)$ of order 0 and repetition 0 and a Zernike moment $Z^B_{11}(i)$ of order 1 and repetition 1 of a pixel point i at the same position in the floating image $I^B(i)$; and step 3: establishing an objective function g(T) according to the local descriptor $ZMLD^A(i)$ of the reference image and the local descriptor $ZMLD^B(i)$ of the floating image; obtaining a transformation parameter according to the objective function, transforming the floating image according to the transformation parameter, and performing an interpolation process on a transformed floating image, thereby obtaining the registration image, wherein the step 2 further comprises the following sub-steps:

step 2-1: obtaining a similarity distance $D^A_{00}(i)$ corresponding to the Zernike moment of order 0 and repetition 0 and a similarity distance $D^A_{11}(i)$ corresponding to the Zernike moment of order 1 and repetition 1 of the pixel point i to other pixel points in an image patch centered at the pixel point i in the reference image; simultaneously, obtaining a similarity distance $D^B_{00}(i)$ corresponding to the Zernike moment of order 0 and repetition 0 and a similarity distance $D^B_{11}(i)$ corresponding to the Zernike moment of order 1 and repetition 1 of the pixel point i to other pixel points in an image patch centered at the pixel point i in the floating image;

step 2-2: obtaining the local descriptor $ZMLD^A(i)$ of the reference image and the local descriptor $ZMLD^B(i)$ of the floating image, $$ZMLD^A(i) = \exp\left(-\frac{D^A_{00}(i)}{h^A_{00}(i)} - \frac{D^A_{11}(i)}{h^A_{11}(i)}\right),$$

$$ZMLD^B(i) = \exp\left(-\frac{D^B_{00}(i)}{h^B_{00}(i)} - \frac{D^B_{11}(i)}{h^B_{11}(i)}\right),$$

wherein $h^A_{00}(i)$, $h^A_{11}(i)$, $h^B_{00}(i)$ and $h^B_{11}(i)$ are decay parameters.

2. The registration method of claim 1, wherein in the step 2-1, the image patches in the step 2-2 all have a side length of 3, and in the step 2-2, $$h_{00}^A(i) = \{\sigma_{00}^A(i) + c_1 \cdot 1.4826 MED[|\sigma_{00}^A(i) - MED(|\sigma_{00}^A(i)|)|]\}^2,$$

$$\sigma_{00}^A(i) = c_2 \frac{|8|Z_{00}^A(i)| - \sum |Z_{00}^A(j)||}{\sqrt{72}},$$

$$h_{11}^A(i) = \{\sigma_{11}^A(i) + c_1 \cdot 1.4826 MED[|\sigma_{11}^A(i) - MED(|\sigma_{11}^A(i)|)|]\}^2,$$

$$\sigma_{11}^A(i) = c_2 \frac{|8|Z_{11}^A(i)| - \sum |Z_{11}^A(j)||}{\sqrt{72}},$$

$$h_{00}^B(i) = \{\sigma_{00}^B(i) + c_1 \cdot 1.4826 MED[|\sigma_{00}^B(i) - MED(|\sigma_{00}^B(i)|)|]\}^2,$$

$$\sigma_{00}^B(i) = c_2 \frac{|8|Z_{00}^B(i)| - \sum |Z_{00}^B(j)||}{\sqrt{72}},$$

$$h_{11}^B(i) = \{\sigma_{11}^B(i) + c_1 \cdot 1.4826 MED[|\sigma_{11}^B(i) - MED(|\sigma_{11}^B(i)|)|]\}^2,$$

$$\sigma_{11}^B(i) = c_2 \frac{|8|Z_{11}^B(i)| - \sum |Z_{11}^B(j)||}{\sqrt{72}},$$

wherein MED(•) represents a median operator, $c_1$ and $c_2$ are constants of 0.5-1, and j is any pixel point in the image patch centered at the pixel point i.

3. A registration system based on the registration method of claim 2, wherein the registration system comprises a first Zernike moment module, a first descriptor module, a second Zernike moment module, a second descriptor module and a registration module;
  wherein the first Zernike moment module is configured to obtain Zernike moments of order 0 and repetition 0 and Zernike moments of order 1 and repetition 1 of a reference image and output them to the first descriptor module, and the first descriptor module is configured to obtain local descriptors of the reference image and output them to the registration module,
  wherein the second Zernike moment module is configured to obtain Zernike moments of order 0 and repetition 0 and Zernike moments of order 1 and repetition 1 of a floating image and output them to the second descriptor module, and the second descriptor module is configured to obtain local descriptors of the floating image and output them to the registration module,
  wherein the registration module is configured to obtain a registration image.

4. The registration method of claim 1, wherein the step 3 specifically comprises the following sub-steps:
  step 3-1: establishing the objective function $g(T_\tau)=SSD+\alpha R(T_\tau)$, wherein SSD represents a sum of squared differences between the local descriptors $ZMLD^A(i)$ and $ZMLD^B(i)$, $\alpha$ ($0<\alpha<1$) is a constant, $R(T_\tau)$ represents a regularization term, and the number of iterations $\tau=1$; iteratively solving the objective function $g(T_\tau)$ to obtain the transformation parameter $T_\tau$;
  step 3-2: transforming the local descriptor $ZMLD^B(i)$ of the floating image according to the transformation parameter $T_\tau$, performing the interpolation process on the transformed local descriptor, and updating the original local descriptor $ZMLD^B(i)$ with the local descriptor subjected to the interpolation process, $\tau=\tau+1$; iteratively solving the objective function $g(T_\tau)$ to obtain a transform parameter $T_\tau$;
  step 3-3: if the number of iterations $\tau$ is greater than or equal to a threshold $\xi$ of the number of iterations and $g(T_\tau) \geq g(T_{\tau-1})$, transforming the floating image according to the transformation parameter $T_\tau$, and performing the interpolation process on the transformed floating image to obtain the registration image; otherwise, returning to the step 3-2.

5. The registration method of claim 4, wherein the similarity metric SSD in the step 3-1 is expressed as:

$$SSD = \frac{\sum_{i=1}^{M} [ZMLD^A(i) - ZMLD^B(i)]^2}{M}.$$

6. A registration system based on the registration method of claim 5, wherein the registration system comprises a first Zernike moment module, a first descriptor module, a second Zernike moment module, a second descriptor module and a registration module;
  wherein the first Zernike moment module is configured to obtain Zernike moments of order 0 and repetition 0 and Zernike moments of order 1 and repetition 1 of a reference image and output them to the first descriptor module, and the first descriptor module is configured to obtain local descriptors of the reference image and output them to the registration module,
  wherein the second Zernike moment module is configured to obtain Zernike moments of order 0 and repetition 0 and Zernike moments of order 1 and repetition 1 of a floating image and output them to the second descriptor module, and the second descriptor module is configured to obtain local descriptors of the floating image and output them to the registration module,
  wherein the registration module is configured to obtain a registration image.

7. The registration method of claim 4, wherein an iteration solution is performed by a limited memory Broyden-Fletcher-Goldfarb-Shanno method or a gradient descent method, a transformation is performed by using a B-spline Free-form Deformation model, and the interpolation process is performed by a bilinear interpolation method or a B-spline interpolation method.

8. A registration system based on the registration method of claim 7, wherein the registration system comprises a first Zernike moment module, a first descriptor module, a second Zernike moment module, a second descriptor module and a registration module;
  wherein the first Zernike moment module is configured to obtain Zernike moments of order 0 and repetition 0 and Zernike moments of order 1 and repetition 1 of a reference image and output them to the first descriptor module, and the first descriptor module is configured to obtain local descriptors of the reference image and output them to the registration module,
  wherein the second Zernike moment module is configured to obtain Zernike moments of order 0 and repetition 0 and Zernike moments of order 1 and repetition 1 of a floating image and output them to the second descriptor module, and the second descriptor module is configured to obtain local descriptors of the floating image and output them to the registration module,
  wherein the registration module is configured to obtain a registration image.

9. A registration system based on the registration method of claim 4, wherein the registration system comprises a first Zernike moment module, a first descriptor module, a second Zernike moment module, a second descriptor module and a registration module;
  wherein the first Zernike moment module is configured to obtain Zernike moments of order 0 and repetition 0 and Zernike moments of order 1 and repetition 1 of a reference image and output them to the first descriptor module, and the first descriptor module is configured to obtain local descriptors of the reference image and output them to the registration module, wherein the second Zernike moment module is configured to obtain Zernike moments of order 0 and repetition 0 and Zernike moments of order 1 and repetition 1 of a floating image and output them to the second descriptor module, and the second descriptor module is configured to obtain local descriptors of the floating image and output them to the registration module, wherein the registration module is configured to obtain a registration image.

10. A registration system based on the registration method of claim 1, wherein the registration system comprises a first Zernike moment module, a first descriptor module, a second Zernike moment module, a second descriptor module and a registration module;

wherein the first Zernike moment module is configured to obtain Zernike moments of order 0 and repetition 0 and Zernike moments of order 1 and repetition 1 of a reference image and output them to the first descriptor module, and the first descriptor module is configured to obtain local descriptors of the reference image and output them to the registration module, wherein the second Zernike moment module is configured to obtain Zernike moments of order 0 and repetition 0 and Zernike moments of order 1 and repetition 1 of a floating image and output them to the second descriptor module, and the second descriptor module is configured to obtain local descriptors of the floating image and output them to the registration module, wherein the registration module is configured to obtain a registration image.

11. The registration system of claim 10, wherein the registration module includes a solving unit and a determining unit, in which the solving unit is configured to construct an objective function according to the local descriptors of the reference image and the floating image, obtain a transformation parameter and output the transformation parameter to the determining unit, and the determining unit is configured to determine whether the objective function meets an iteration stopping criterion, if not, the local descriptor of the floating image is transformed according to the transformation parameter, interpolation process is performed on the transformed local descriptor, the original local descriptor of the floating image is updated with the local descriptor of the floating image subjected to the interpolation process; if yes, the floating image is transformed according to the transformation parameter and interpolation process is performed on the floating image to obtain the registration image.

* * * * *